(12) United States Patent
Lai et al.

(10) Patent No.: US 6,382,793 B1
(45) Date of Patent: May 7, 2002

(54) METHOD AND APPARATUS FOR MEASURING A WAVEFRONT

(75) Inventors: Ming Lai, Dublin; Ning Y. Chan, Berkeley; Jay Wei, Fremont, all of CA (US)

(73) Assignee: Carl Zeiss, Inc., Thornwood, NY (US)

( * ) Notice: Subject to any disclaimer, the term of this patent is extended or adjusted under 35 U.S.C. 154(b) by 0 days.

(21) Appl. No.: 09/575,421

(22) Filed: May 20, 2000

(51) Int. Cl.⁷ ................................................. A61B 3/14
(52) U.S. Cl. ....................................................... 351/206
(58) Field of Search ................................. 351/205, 206, 351/211, 212, 214, 246; 356/121, 127; 250/201.9, 208.1, 208.2, 204

(56) References Cited

U.S. PATENT DOCUMENTS

| | | | |
|---|---|---|---|
| 4,180,325 A | 12/1979 | Humphrey | 356/127 |
| 4,182,572 A | 1/1980 | Humphrey | 356/127 |
| 4,199,816 A | 4/1980 | Humphrey | 364/571 |
| 4,490,039 A | 12/1984 | Bruckler et al. | 356/121 |
| 5,208,619 A | 5/1993 | Campbell | 351/211 |
| 5,493,391 A * | 2/1996 | Neal et al. | 356/121 |
| 5,629,765 A | 5/1997 | Schmutz | 356/121 |
| 5,737,059 A | 4/1998 | Tanaka | 351/214 |
| 5,777,719 A | 7/1998 | Williams et al. | 351/212 |
| 5,949,521 A | 9/1999 | Williams et al. | 351/246 |

FOREIGN PATENT DOCUMENTS

WO   27334   6/1999   ............. G01J/1/00

OTHER PUBLICATIONS

"Objective measurement of wave aberrations of the human eye with the use of a Hartmann–Shack wave–front sensor," J. Opt. Soc. Am. A, vol. 11, No. 7, pp. 1949–1957, Jul. 1994.

* cited by examiner

*Primary Examiner*—George Manuel
(74) *Attorney, Agent, or Firm*—Michael B. Einschlag

(57) ABSTRACT

Embodiments of the present invention provide method and apparatus for measuring a wavefront of a beam of radiation. In particular, one embodiment of the present invention is an apparatus for measuring a wavefront of a beam of radiation at a first plane which includes: (a) relay optics adapted to relay the wavefront from the first plane to a second plane; (b) a moving boundary locus apparatus disposed between the first and second planes; (c) a two-dimensional photodetector array comprising—at least 4×4 photodetector elements disposed in the second plane, wherein each photodetector element produces a time varying signal in response to movement of a portion of the moving boundary locus apparatus; (d) a synchronizer adapted to synchronize each of the time varying signals with a position of the portion of the moving boundary locus apparatus; and (e) an analyzer, responsive to synchronized time varying signals output from the synchronizer, to measure the wavefront of the beam.

16 Claims, 5 Drawing Sheets

METHOD AND APPARATUS FOR MEASURING A WAVEFRONT

TECHNICAL FIELD OF THE INVENTION

The present invention pertains to method and apparatus for measuring a wavefront of a beam of radiation. In particular, the present invention pertains to method and apparatus for measuring a wavefront of a beam of radiation having a large slope variation for use in applications including, but not limited to, characterization of optical quality of optical elements and systems, and diagnosis of eye function.

BACKGROUND OF THE INVENTION

As is well known, a wavefront sensor provides comprehensive measurements relating to a wavefront of a beam of radiation, and can therefore be used to characterize the optical quality of optical elements and systems. Traditionally, such wavefront sensors include an interferometer and, recently, much use has been made of a "Hartmann-Shack" sensor.

An interferometer-based wavefront sensor requires a high quality reference beam having substantial coherence length and sub-wavelength stability. A Hartmann-Shack-based wavefront sensor is preferred over the interferometer-based wavefront sensor because: (a) the Hartmann-Shack-based wavefront sensor does not require a reference beam; and (b) it is easier to use outside of a laboratory environment. As is well known, the Hartmann-Shack-based wavefront sensor comprises a lenslet array disposed in front of a CCD camera, and it measures the tilt distribution of ray bundles associated with the wavefront to be measured. A perceived advantage of the Hartmann-Shack-based wavefront sensor is its simplicity and reliability. Among the key parameters which are involved in using a Hartmann-Shack-based wavefront sensor are: (a) sensitivity to resolve minimum wavefront tilt; (b) dynamic range to cover the maximum wavefront tilt; (c) spatial resolution; and (d) sampling time.

The Hartmann-Shack-based wavefront sensor has been used for adaptive optics applications in astronomy. In such applications, a short sampling time (for example, less than 30 ms) is desirable to follow fluctuations caused by air turbulence, and small dynamic ranges (for example, less than 1 mR) are sufficient. However, for other types of applications, much larger dynamic ranges are required, while relatively longer sampling times can be acceptable. One example of such other applications is a comprehensive measurement of eye aberration errors useful for eye diagnosis. In particular, wavefront measurement data can be used to guide photorefractive surgery to achieve optimal results from surgery. In such an application, a wavefront measurement apparatus is expected to measure a wavefront over a dynamic range of ±60 mR with a tilt resolution of 0.1 mR. Such a dynamic range is well beyond the results obtainable from current Hartmann-Shack-based wavefront sensors.

As one can readily appreciate from the above, a need exists in the art for method and apparatus for measuring a wavefront over a wide dynamic range, and with small tilt resolution.

SUMMARY OF THE INVENTION

Embodiments of the present invention advantageously satisfy the above-identified need in the art, and provide method and apparatus for measuring a wavefront over a wide dynamic range, and with small tilt resolution.

Specifically, one embodiment of the present invention is an apparatus for measuring a wavefront of a beam of radiation at a plane which comprises: (a) a moving boundary locus apparatus disposed before the plane; (b) a two-dimensional photodetector array comprising a plurality of photodetector elements disposed in the plane, wherein each photodetector element produces a time varying signal in response to movement of a portion of the moving boundary locus apparatus; (c) a synchronizer adapted to synchronize each of the time varying signals with a position of the portion of the moving boundary locus apparatus; and (d) an analyzer, responsive to synchronized time varying signals output from the synchronizer, to measure the wavefront of the beam.

DETAILED DESCRIPTION

Figure 1:
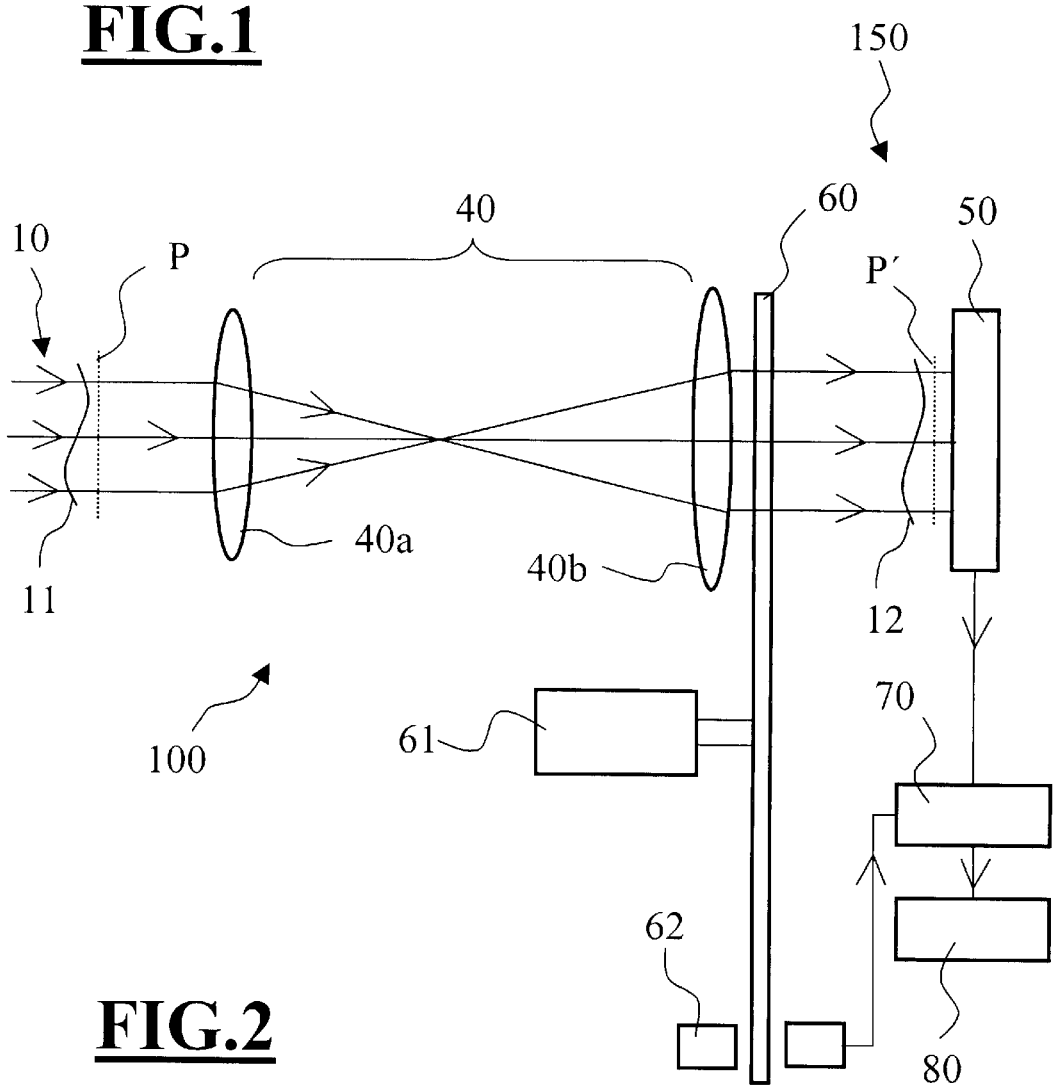
FIG. 1 shows a block diagram of a wavefront measurement apparatus that is fabricated in accordance with one embodiment of the present invention.

FIG. 1 shows a block diagram of wavefront measurement apparatus 100 that is fabricated in accordance with the present invention. As shown in FIG. 1, wavefront measurement apparatus 100 comprises relay optics assembly 40 and wavefront sensing assembly 150.

As further shown in FIG. 1, relay optic assembly 40 comprises lens systems 40a and 40b, which lens systems 40a and 40b may each comprise one or more lenses. Wavefront sensing assembly 150 comprises two-dimensional photodetector array 50, moving boundary locus apparatus 60, synchronizer 70, and analyzer 80.

As shown in FIG. 1, radiation beam 10 impinges upon wavefront measurement apparatus 100, and wavefront 11 of beam of radiation 10 is to be measured at plane P. Relay optics assembly 40 relays wavefront 11 to plane P', which plane P' is conjugate to plane P. As is well known to those of ordinary skill in the art, wavefront 12 at plane P' is identical to wavefront 11 at plane P up to a predetermined scale factor when lens systems 40a and 40b are arranged in a confocal configuration.

In accordance with the embodiment of the present invention shown in FIG. 1, two-dimensional photodetector array 50 comprises a matrix of photodetector elements which is disposed in plane P' to receive radiation from beam 10. In accordance with this embodiment, each photodetector element receives a beam segment from beam 10, and thereby wavefront 12 is divided into wavefront segments. As is well known to those of ordinary skill in the art, wavefront 12 at plane P' can be measured if each wavefront segment is measured accurately.

It should be clear to those of ordinary skill in the art that relay optics assembly 40 provides for convenient use of apparatus 100, but that relay optics assembly 40 is not a necessary part of each embodiment of the present invention. For example, when apparatus 100 is used where there is a substantial amount of working space in front of plane P, measurements can be made directly at plane P, i.e., two-dimensional photodetector array 50 may be disposed at plane P.

As is well known to those of ordinary skill in the art, each beam segment of wavefront 12 can be associated with a ray bundle. Further, in accordance with this embodiment of the present invention, the average tilt of the ray bundle is taken to be perpendicular to the mean slope of the wavefront segment of the corresponding beam segment. The average tilt of the ray bundle can be determined using centroid positions of the two ends of the ray bundle. In accordance with this embodiment of the present invention, one end of each ray bundle is determined by the centroid position of a photodetector element in photodetector array 50, and the other end of each ray bundle is determined by moving boundary locus apparatus 60. This is contrasted with a Hartmann-Shack wavefront sensor where one end of each ray bundle is determined by a lenslet element in a lenslet array, and the other end of each ray bundle is determined by a CCD camera.

Figure 2:
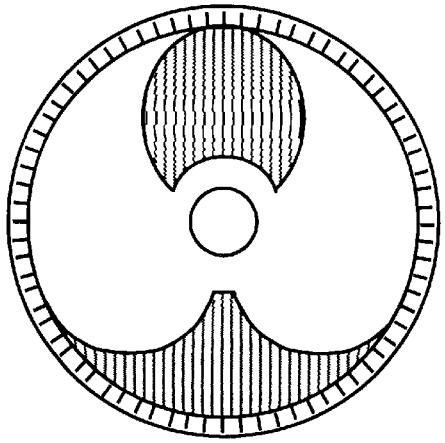
FIG. 2 shows a block diagram of a moving boundary locus apparatus in the prior art that is used to fabricate a preferred embodiment of the present invention.

Moving boundary locus apparatus 60 is fabricated in accordance with a teaching regarding a moving boundary locus apparatus that is disclosed in U.S. Pat. No. 4,180,325 ('325 patent), which '325 patent is incorporated by reference herein. The '325 patent teaches how such a moving boundary locus apparatus can be used, together with an edge detector and a synchronizer, to determine a centroid of a ray bundle falling onto photodetector element of photodetector array 50. As shown in FIG. 1, motor 61 rotates moving boundary locus apparatus 60, and edge detector 62 (in accordance with the teaching of the '325 patent) monitors an angular position of moving boundary locus apparatus 60. FIG. 2 shows one embodiment of moving boundary locus apparatus 60 that is fabricated in accordance with the teaching of the '325 patent. Many other embodiments of moving boundary locus apparatus 60 may be fabricated by those of ordinary skill in the art in accordance with the teaching of the '325 patent.

In accordance with this embodiment of the present invention, output from each photodetector element of photodetector array 50 is applied as input to an independent amplifier. As moving boundary locus apparatus 60 moves (for example, rotates for the embodiment shown in FIG. 2), each photodetector element produces a time varying signal, which time varying signal is synchronized with a spatial position (for example, the angular position for the embodiment shown in FIG. 2) of moving boundary locus apparatus 60 by edge detector 62 and synchronizer 70. The synchronized time varying signals output from synchronizer 70 are applied as input to analyzer 80 (for example, a computer such as a personal computer). Using timing signatures of the synchronized time varying signals, analyzer 80 calculates a centroid position of one end of ray bundles falling onto corresponding photodetector elements in accordance with the teaching of the '325 patent. Embodiments of synchronizer 70 are fabricated in accordance with the teachings of the '325 patent.

In accordance with this embodiment of the present invention, each photodetector element receives a beam segment, and thus defines the other end of a ray bundle falling onto the photodetector element. For example, the x, y, z position of a centroid of the photodetector element determines one end of the ray bundle. In a preferred embodiment of the present invention, each photodetector element of two-dimensional photodetector array 50 is about 1×1 mm, and such a photodetector array is, for example, commercially available from Hamamatsu of Japan. Then, analyzer 80 determines the slope of each beam segment using the coordinates of the two ends of each ray bundle.

Finally, in one embodiment, analyzer 80 uses any one of a number of methods that are well known to those of ordinary skill in the art to use the slopes of the beam segments to reconstruct the wavefront of beam 10 at plane P'. For example, in one such embodiment, analyzer 80 fits the slopes of the beam segments to a set of Zernike polynomials to reconstruct the wavefront in accordance with the teaching of an article entitled "Objective measurement of wave aberrations of the human eye with the use of a Hartmann-Shack wave-front sensor" by J. Liang et al., *J. Opt. Soc. Am. A*, Vol. 11, No. 7, July 1994, pp. 1949–1957 (the "Liang article"), which Liang article is incorporated by reference herein. The wavefront of beam 10 is then reconstructed at plane P via a scale factor determined by the relay optics. In accordance with this embodiment of the present invention, photodetector array 50 has at least 4×4 photodetector elements in order to fit coefficients of the first 16 Zernike polynomials. However, a larger array, for example and without limitation, a 10×10 array, is preferred to achieve better spatial resolution and higher accuracy.

Figure 3:
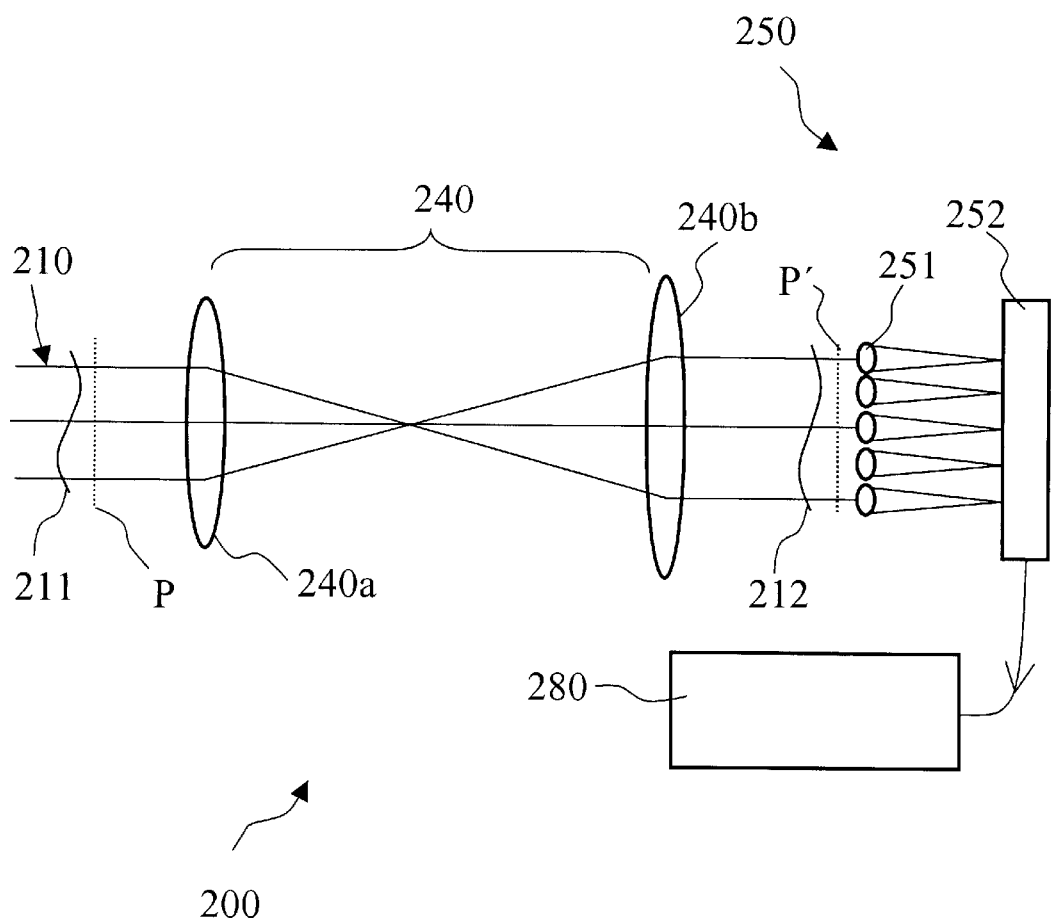
FIG. 3 shows a block diagram of a prior art wavefront measurement apparatus using a Hartmann-Shack sensor.

FIG. 3 shows a block diagram of a prior art wavefront measurement apparatus using a Hartmann-Shack sensor. A comprehensive review of the Hartmann-Shack wavefront sensor, and wavefront reconstruction is found in U.S. Pat. No. 5,777,719. As shown in FIG. 3, prior art wavefront sensor 200 comprises relay optics assembly 240 (includes lens systems 240a and 240b) and Hartmann-Shack sensor 250 (includes lenslet array 251 disposed in front of CCD camera 252).

As shown in FIG. 3, radiation beam 210 impinges upon wavefront sensor 200, and wavefront 211 of beam of radiation 210 is to be measured at plane P. Relay optics assembly 240 relays wavefront 211 to plane P', which plane P' is conjugate to plane P. As further shown in FIG. 3, lenslet array 251 is disposed in plane P' and CCD camera 252 is located in the focal plane of lenslet array 251. As is well known, lenslet array 251 divides a beam of radiation onto an array of beam segments, and focuses each beam segment onto CCD camera 252 (each lenslet element is related to a beam segment and to a focal spot on CCD camera 252). In wavefront sensor 200, the position of a lenslet element, and the centroid position of the corresponding focal spot determine the centroid of a ray bundle passing through the lenslet element. The centroid of the ray bundle is then used to resolve the mean slope of the beam segment. Analyzer 280, for example, a personal computer, fits the slopes of the beam segments to a set of Zernike polynomials to reconstruct the wavefront of beam 210 in accordance with the method disclosed in the Liang article.

As one can readily appreciate from comparing FIGS. 1 and 3, in inventive wavefront measurement apparatus 100, two-dimensional photodetector array 50 is disposed at plane P', and as a consequence, moving boundary locus 60 determines an end position of a ray bundle. In contrast, in prior art Hartmann-Shack wavefront sensor 200, lenslet array 251 is disposed at plane P', and as a consequence, CCD camera 252 determines an end position of a ray bundle. Because of this difference, inventive wavefront measurement apparatus 100 has advantages over prior art Hartmann-Shack wavefront sensor 200 that are best understood in conjunction with FIGS. 4A–5E.

Figure 4A:
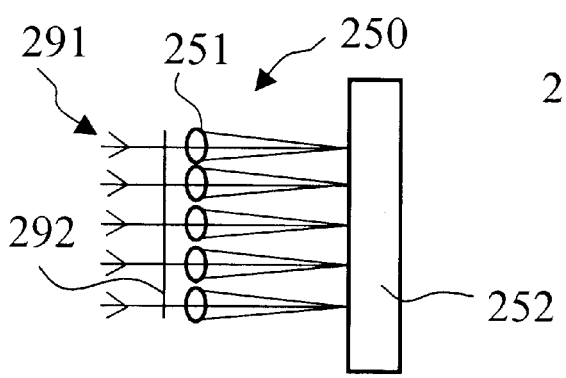
FIGS. 4A–4D illustrate wavefront measurements made with a prior art Hartmann-Shack sensor for: (a) a flat wavefront, (b) a converging wavefront, (c) a diverging wavefront, and (d) a flat-converging wavefront, respectively.
Figure 4B:
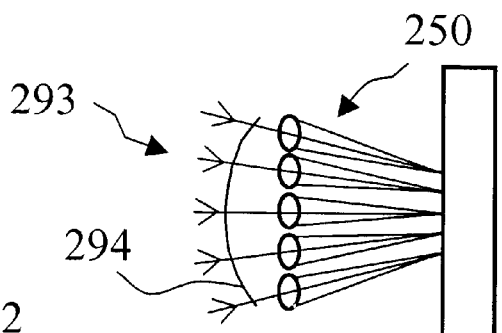
Figure 4C:
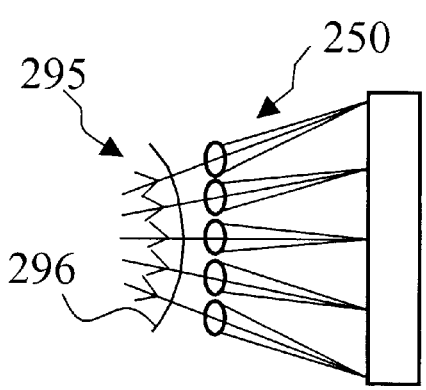
Figure 4D:
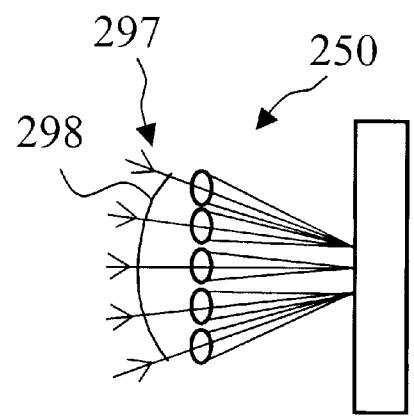

FIG. 4A illustrates a wavefront measurement made with prior art Hartmann-Shack sensor 200 for flat wavefront 291. As shown in FIG. 4A, a ray bundle that passes through each lenslet element of lenslet array 251 is focused at one spot on CCD 252, and the separation between focal spots is equal to the spacing between the lenslet elements. FIG. 4B illustrates a wavefront measurement made with prior art Hartmann-Shack sensor 200 for converging wavefront 294. As shown in FIG. 4B, in this case, the separation between focal spots is smaller than the spacing between lenslet elements, and as a result, the dynamic range of tilt measurement of prior art sensor 200 is limited by overlapping of focal spots. FIG. 4C illustrates a wavefront measurement made with prior art Hartmann-Shack sensor 200 for diverging wavefront 296. As shown in FIG. 4C, in this case, the separation between focal spots is larger than the spacing between lenslet elements, and as a result, the dynamic range of tilt measurement of prior art sensor 200 is limited by a size of CCD camera 252. Lastly, FIG. 4D illustrates a wavefront measurement made with prior art Hartmann-Shack sensor 200 for flat-converging wavefront 298 (this is a typical wavefront obtained from a patient after photorefractive surgery to correct myopia in a central portion of the eye). As shown in FIG. 4D, in this case, focal spots from the central, flat portion of wavefront 298 are uniformly distributed while focal spots from an edge of wavefront 298 tilt toward the center. As a result, the dynamic range of tilt measurement is limited by overlapping of focal spots.

Figure 5A:
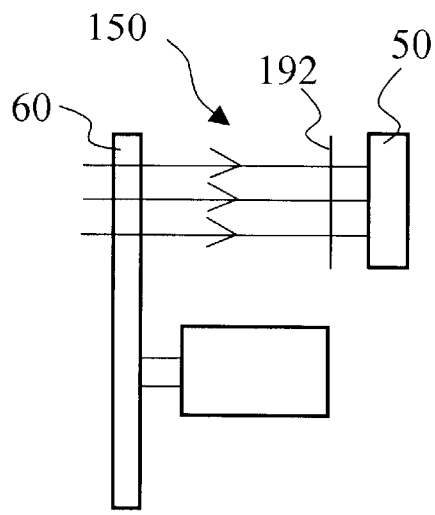
FIGS. 5A–5E illustrate wavefront measurements made with an embodiment of the present invention for: (a) a flat wavefront, (b) a converging wavefront, (c) a diverging wavefront; (d) a flat-converging wavefront, and, (e) a flat-diverging wavefront, respectively.
Figure 5B:
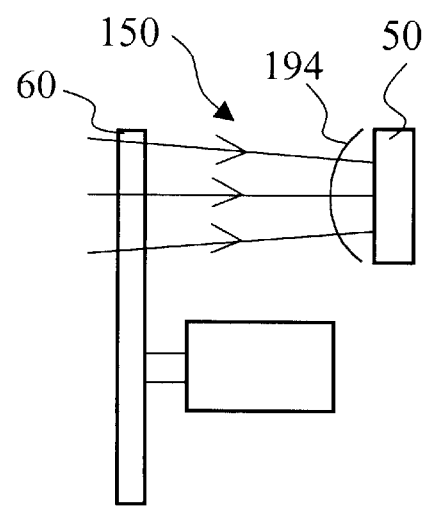
Figure 5C:
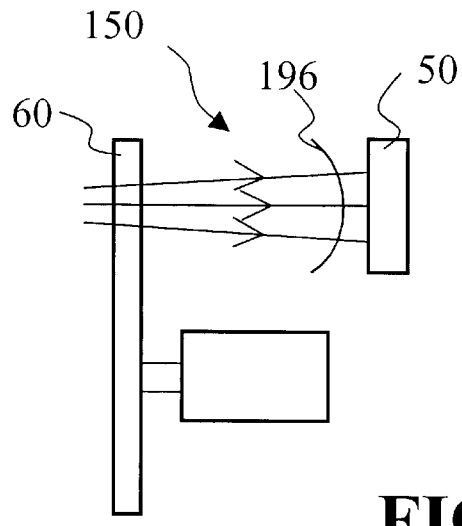
Figure 5D:
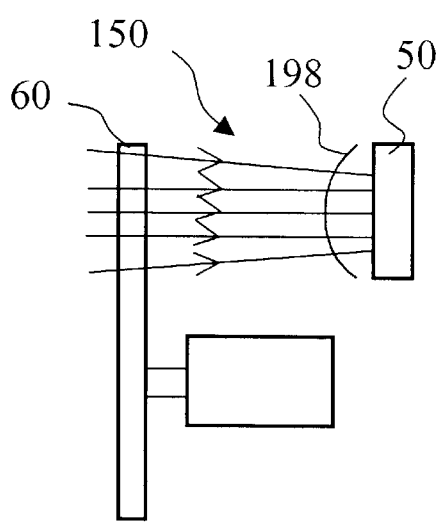
Figure 5E:
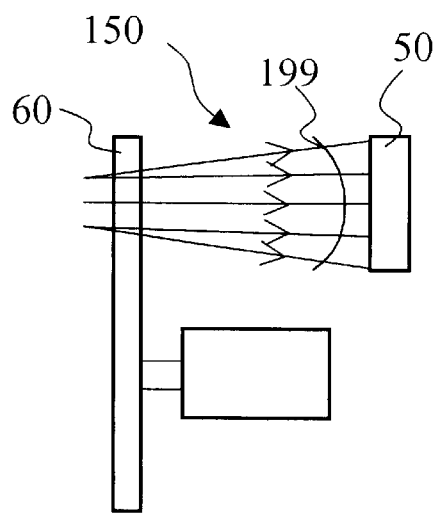

FIG. 5A illustrates a wavefront measurement made with wavefront measurement apparatus 100 for flat wavefront 192. FIG. 5B illustrates a wavefront measurement made with wavefront measurement apparatus 100 for converging wavefront 194. FIG. 5C illustrates a wavefront measurement made with wavefront measurement apparatus 100 for diverging wavefront 196. FIG. 5D illustrates a wavefront measurement made with wavefront measurement apparatus 100 for flat-converging wavefront 198. Lastly, FIG. 5E illustrates a wavefront measurement made with wavefront measurement apparatus 100 for flat-diverging wavefront 199.

As seen in FIGS. 5A–5E, the intensity distribution on photodetector array 50 is approximately uniform. As was described above, for a ray bundle associated with any beam segment, a photodetector element of photodetector array 50 defines a position at one end of the ray bundle, and moving boundary locus apparatus 60 detects a centroid position at the other end of the ray bundle. Advantageously, in accordance with this embodiment of the present invention, detection relating to a ray bundle associated with one beam segment by moving boundary locus apparatus 60 is independent of detection relating to ray bundles associated with other beam segments. Therefore, even though the ray bundles associated with different beam segments may overlap with each other on the plane of moving boundary locus 60, precise measurement is not interfered with. This advantageous feature of embodiments of the present invention enables measurement of wavefront having large tilt variation. In addition, the distance between photodetector array 50 and moving boundary locus 60 can be big in comparison with the distance between lenslet 251 and CCD camera 253 of Hartmann-Shack wavefront sensor 200. This advantageous feature of embodiments of the present invention enables better resolution in tilt measurement than that provided by Hartmann-Shack wavefront sensor 200.

Figure 6:
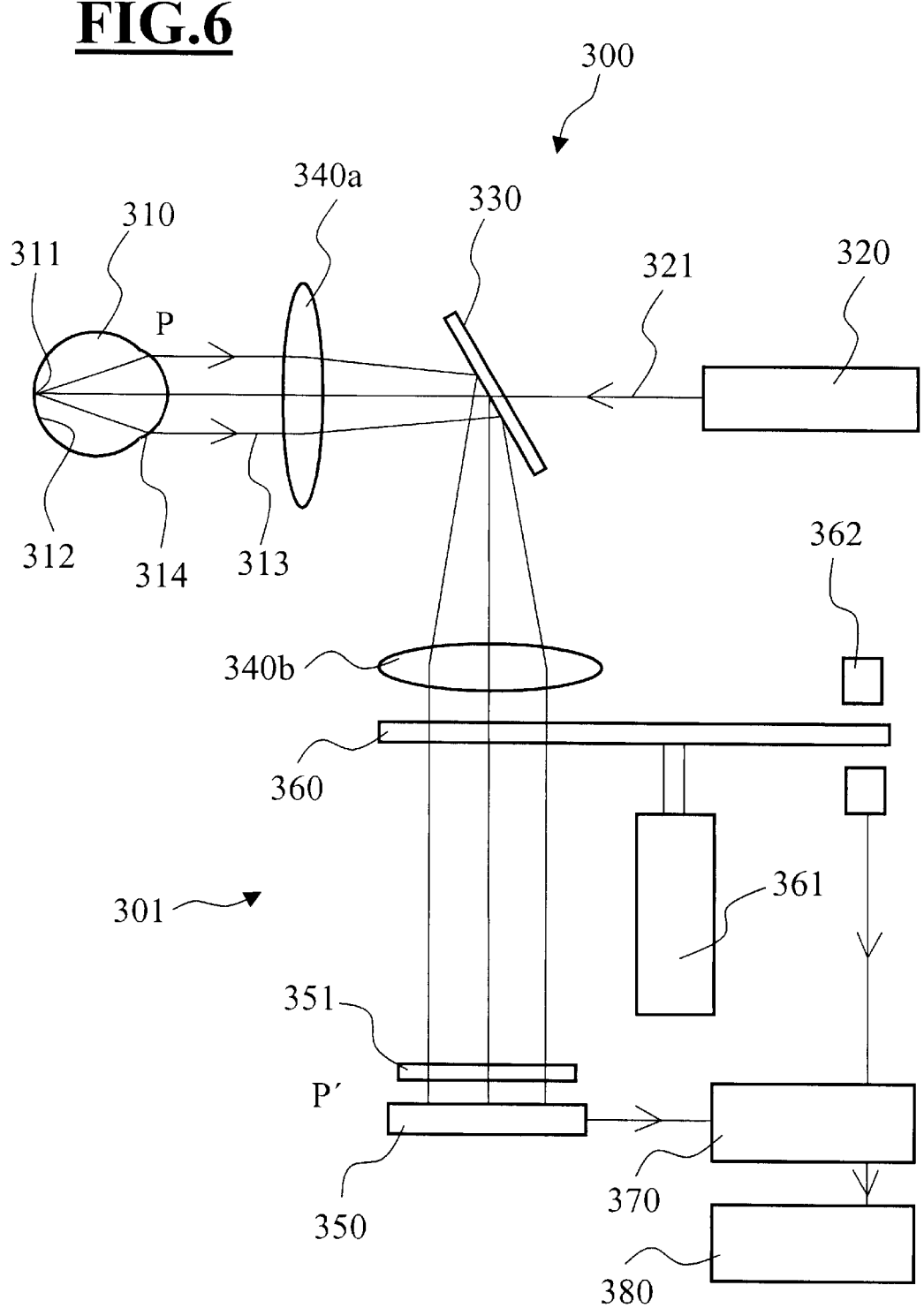
FIG. 6 shows a block diagram of an embodiment of the present invention for use in measuring eye aberration.

FIG. 6 shows a block diagram of wavefront aberration measurement apparatus 300 which is fabricated in accordance with the present invention for use in measuring eye aberration. As shown in FIG. 6, wavefront aberration measurement apparatus 300 comprises probe beam projector 320, dichroic beamsplitter 330, a relay optics assembly comprised of relay optics system 340a and relay optics system 340b; and wavefront sensing assembly 301. Relay optics systems 340a and 340b could each comprise one or more lenses. As further shown in FIG. 6, wavefront sensing assembly 301 comprises two-dimensional photodetector array 350, moving boundary locus apparatus 360, synchronizer 370, and analyzer 380.

In accordance with this embodiment of the present invention, probe beam projector 320 projects linearly polarized probe beam 321 which produces a small illumination spot 311 on retina 312. Radiation beam 313 scattered from spot 311 is relayed by the relay optics assembly (comprised of relay optics system 340a and relay optics system 340b) onto photodetector array 350 which is disposed at plane P', which plane P' is conjugate to pupil plane P. Polarizing beamsplitter 351 is located in front of photodetector array 350 to allow only a depolarized portion of scattered beam 313 to pass therethrough (polarizing beamsplitter 351 rejects reflections from relay optics system 340a, cornea 314, and retina 312). The wavefront of scattered beam 313 is then reconstructed in the manner described in detail above by wavefront sensing assembly 301. Finally, eye aberrations are calculated by analyzer 380 in accordance with any one of a number of methods that are well known to those of ordinary skill in the art using the reconstructed wavefront. For example, one such method is disclosed in a publication of Frey et al. on Jun. 3, 1999, WO 99/27334 entitled "Objective Measurement and Correction of Optical Systems Using Wavefront Analysis" wherein distortions of the wavefront are taken as an estimate of the aberrations, which publication is incorporated by reference herein (see also the Liang article).

The range and resolution of wavefront tilt measurements obtained using embodiments of the present invention can be estimated as follows. Assume that an aperture of about 30 mm is provided in moving boundary locus apparatus 60, and a spacing of about 100 mm exists between moving boundary locus apparatus 60 and photodetector array 50. It is known in the art that the moving boundary locus technique can resolve the centroid position of an end of a ray bundle to better than ten (10) microns. The full cone angle that ray bundles may pass through moving boundary locus apparatus 60 and fall onto photodetector array 50 is approximately 300 m-Radians (30 mm/100 mm). Thus, the maximum tilt angle that can be measured is ±150 m-Radians and the tilt resolution is approximately 0.1 m Radian (10 microns/100 mm).

Eye aberration can be characterized by the wavefront of scattered beam 313. As such, a wavefront tilt measurement of about ±80 m-Radian is desirable to cover ±20 D of refractive error over an 8 mm pupil. Besides, a resolution of ±0.1 D or better is expected in a refractive error measurement. This translates to ±0.4 m-Radian or better in wavefront tilt measurement. As estimated above, wavefront measurement in accordance with embodiments of the present invention can meet these requirements for eye aberration diagnosis.

Those skilled in the art will recognize that the foregoing description has been presented for the sake of illustration and description only. As such, it is not intended to be exhaustive or to limit the invention to the precise form disclosed.

What is claimed is:

1. Apparatus to measure a wavefront of a beam of radiation at a plane, which apparatus comprises:
   a moving boundary locus apparatus disposed before the plane;
   a two-dimensional photodetector array comprising a plurality of photodetector elements disposed in the plane, wherein each photodetector element produces a time varying signal in response to movement of a portion of the moving boundary locus apparatus;
   a synchronizer adapted to synchronize each of the time varying signals with a position of the portion of the moving boundary locus apparatus; and
   an analyzer, responsive to synchronized time varying signal output from the synchronizer, adapted to measure the wavefront of the beam.

2. The apparatus of claim 1 wherein the analyzer is adapted to determine a slope of beam segments associated with photodetector elements, and therefrom, to measure the wavefront of the beam.

3. The apparatus of claim 1 wherein the two-dimensional photodetector array comprises at least a four by four array of photodetector elements.

4. The apparatus of claim 1 wherein the moving boundary locus apparatus comprises a chopper disk.

5. The apparatus of claim 1 wherein the analyzer, responsive to the measurements, is further adapted to reconstruct the wavefront.

6. Apparatus for measuring a wavefront of a beam of radiation at a first plane which comprises:
   relay optics adapted to relay the wavefront from the first plane to a second plane;
   a moving boundary locus apparatus disposed between the first and second planes;
   a two-dimensional photodetector array comprising a plurality of photodetector elements disposed in the second plane, wherein each photodetector element produces a time varying signal in response to movement of a portion of the moving boundary locus apparatus;
   a synchronizer adapted to synchronize each of the time varying signals with a position of the portion of the moving boundary locus apparatus; and
   an analyzer, responsive to synchronized time varying signal output from the synchronizer, adapted to measure the wavefront of the beam.

7. The apparatus of claim 6 wherein the analyzer is adapted to determine a slope of beam segments associated with photodetector elements, and therefrom, to measure the wavefront of the beam.

8. The apparatus of claim 6 wherein the relay optics comprises a pair of lens systems arranged in a confocal configuration.

9. The apparatus of claim 6 wherein the two-dimensional photodetector array comprises at least a four by four array of photodetector elements.

10. The apparatus of claim 6 wherein the moving boundary locus apparatus comprises a chopper disk.

11. The apparatus of claim 6 wherein the analyzer, responsive to the measurements, is further adapted to reconstruct the wavefront.

12. A method for measuring a wavefront of a beam of radiation at a plane which comprises the steps of:
   generating a time varying signal for each of a plurality of photodetector elements which comprise a two-dimensional photodetector array disposed at the plane using a moving boundary locus apparatus disposed before the plane;
   synchronizing each of the time varying signals with a position of a portion of the moving boundary locus apparatus;
   responsive to the synchronized time varying signals, determining a slope of beam segments associated with corresponding photodetector elements; and
   measuring the wavefront of the beam.

13. A method for measuring a wavefront of a beam of radiation at a first plane which comprises the steps of:
   relaying the wavefront from the first plane to a second plane, at which second plane is disposed a two-dimensional photodetector array comprising a plurality of photodetector elements;
   generating a time varying signal for each of the plurality of photodetector elements using a moving boundary locus apparatus disposed between the first and second planes;
   synchronizing each of the time varying signals with a position of a portion of the moving boundary locus apparatus;
   responsive to the synchronized time varying signals, determining a slope of beam segments associated with corresponding photodetector elements; and
   measuring the wavefront of the beam.

14. Apparatus to measure eye aberrations which comprises:
   a probe beam projector which projects a beam of radiation onto a retina of an eye;
   a relay optics system adapted to relay a wavefront of a scattering beam from an eye pupil plane to a second plane;
   a moving boundary locus apparatus disposed between the eye pupil plane and the second plane;
   a two-dimensional photodetector array comprising a plurality of photodetector elements disposed in the second plane, wherein each photodetector element produces a time varying signal in response to movement of a portion of the moving boundary locus apparatus;
   a synchronizer adapted to synchronize each of the time varying signals with a position of the portion of the moving boundary locus apparatus; and
   an analyzer, responsive to synchronized time varying signal output from the synchronizer, adapted to reconstruct the wavefront.

15. The apparatus of claim 14 wherein the analyzer is further adapted to measure eye aberrations from the reconstructed wavefront.

16. The apparatus of claim 15 wherein:
   the probe beam projector projects a linearly polarized beam through a beamsplitter disposed within the relay optics system; and
   wherein the apparatus further comprises a polarizing beamsplitter disposed before the second plane.

* * * * *